United States Patent [19]

Beriger

[11] 4,073,932
[45] Feb. 14, 1978

[54] METHOD OF CONTROLLING INSECTS USING 1,3-DIOXIN-4-ONES

[75] Inventor: Ernst Beriger, Allschwil, Switzerland

[73] Assignee: Ciba-Geigy Corporation, Ardsley, N.Y.

[21] Appl. No.: 757,810

[22] Filed: Jan. 10, 1977

[30] Foreign Application Priority Data

Jan. 14, 1976 Switzerland .............................. 397/76
July 22, 1976 Switzerland .......................... 9391/76
Dec. 14, 1976 Switzerland ........................ 15701/76

[51] Int. Cl.² ............................................. A01N 9/28
[52] U.S. Cl. ..................................... 424/279; 424/278
[58] Field of Search ................................. 424/278, 279

[56] References Cited

U.S. PATENT DOCUMENTS

| | | | |
|---|---|---|---|
| 3,351,485 | 11/1967 | Langner ................................. | 424/279 |
| 3,723,468 | 3/1973 | Blumenfeld et al. ................. | 424/278 |
| 3,895,036 | 7/1975 | Gelotte et al. ........................ | 424/278 |
| 3,901,920 | 8/1975 | Lesher et al. ......................... | 424/278 |
| 3,968,233 | 7/1976 | Garzia ................................... | 424/279 |

FOREIGN PATENT DOCUMENTS 2,149,650 12/1973 Germany .............................. 424/278

*Primary Examiner*—Albert T. Meyers
*Assistant Examiner*—D. W. Robinson
*Attorney, Agent, or Firm*—Harry Falber

[57] ABSTRACT

The invention provides a method for controlling insect pests at a locus which comprises applying to said locus a compound of the formula I

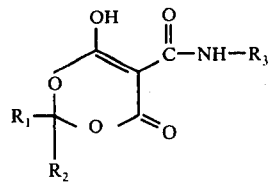

wherein $R_1$ and $R_2$ both represent a methyl group or together represent a tetramethylene or pentamethylene group and $R_3$ represents a phenyl, 3-chlorophenyl, 4-chlorophenyl, 3,4-dichlorophenyl or 4-fluorophenyl group.

8 Claims, No Drawings

METHOD OF CONTROLLING INSECTS USING 1,3-DIOXIN-4-ONES

The present invention provides a method of controlling insects which comprises the use of 2,2-disubstituted-5-phenylcarbamoyl-6-hydroxy-m-dioxin-4-one derivatives.

The 2,2-disubstituted-5-phenylcarbamoyl-6-hydroxy-m-dioxin-4-one derivatives used in accordance with the invention have the formula I

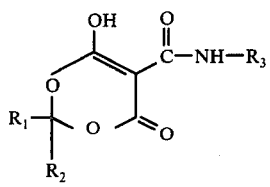

wherein each of $R_1$ and $R_2$ represents a methyl group or together they represent a tetramethylene or pentamethylene group and $R_3$ represents a phenyl, 3-chlorophenyl, 4-chlorophenyl, 3,4-dichlorophenyl or 4-fluorophenyl group.

The compounds of the formula I, can be obtained by methods known per se, for example by (a) reacting an ester of the formula II

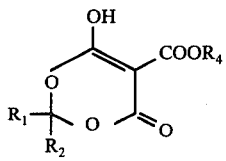

with an aniline of the formula III

(b) reacting a compound of the formula IV

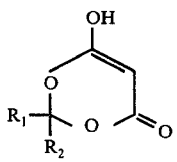

with an isocyanate of the formula V

or (c) treating a compound of the above formula IV with an azide of the formula VI

In the above formulae II to VI, the symbols $R_1$ to $R_3$ are as defined in formula I and $R_4$ represents a $C_1$-$C_4$-alkyl group.

The starting materials of the formulae II and IV are known [see e.g. "Chem. Ber." 94, 929 (1961) and "Tetrahedron Letters" 7, 1 (1959)].

Processes (a) and (c) are preferably carried out at a reaction temperature between 100° and 200° C and process (b) at a reaction temperature between 0° and 200° C. The reactions can be carried out at normal or elevated pressure, optionally in a solvent or diluent which is inert to the reactants and optionally in the presence of a base.

Examples of suitable solvents or diluents for these reactions are: ethers and ethereal compounds, such as dipropyl ether, dioxane, dimethoxyethane and tetrahydrofurane; amides, such as dialkylated carboxamides; aliphatic, aromatic and halogenated hydrocarbons, in particular toluene, xylenes, and chlorobenzene; nitriles, such as acetonitrile; dimethyl sulphoxide; and ketones, such as acetone and methyl ethyl ketone.

Suitable bases are for example: tertiary amines, such as triethylamine, dimethyl aniline, pyridine, picolines and lutidines as well as the hydroxides, oxides, carbonates and bicarbonates of alkali metals and alkaline earth metals, and the alkali metal alcoholates, for example potassium tert. butylate and sodium methylate.

The compounds of the formula I are already known as antimicrobial agents [cf. "Eur. J. Med. Chem. — Chimica Therapeutica" 10 (3), 323–325, (1975)].

According to the present invention, it has now surprisingly been found that the compounds of the formula I possess a good action against insects that are harmful to plants and animals.

In particular, the compounds of the formula I have an effective action against insects of the order Colleoptera, chiefly of the families Chrysomelidae and Curculionidae (for example *Leptinotarsa decemlineata* and *Anthanomus grandis*) and accordingly are suitable for controlling insects in cotton plantations and crops of vegetables. In addition, individual compounds of the formula I act effectively against ectoparasitic insects (for example Lucilia sericata) and insects which are harmful in the sectors of hygiene and storage protection (for example *Musca domestica*), and are especially suitable for treating stored goods and for external application to productive livestock or for treating their environment. The insecticidal action can be substantially broadened and adapted to prevailing circumstances by the addition of other insecticides and/or acaricides.

Examples of suitable additives are: organic phosphorus compounds, nitrophenols and derivatives thereof, formamidines, ureas, pyrethroids, carbamates, and chlorinated hydrocarbons.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsion concentrates, granules, dispersions, sprays, solutions or suspensions such as are commonly employed in application technology.

The compositions according to the invention are obtained in known manner by homogeneously mixing and/or grinding active substances of the formula I with the suitable carriers, with or without the addition of dispersants or solvents which are inert to the active substances.

The compounds of the formula I may be formulated as follows:

Solid formulations:
 Dusts, tracking agents and granules (e.g. coated granules, impregnated granules and homogeneous granules);

Liquid formulations:
a. active substance concentrates which are dispersible in water: wettable powders, pastes, emulsions;
b. solutions.

The content of active substance in the above described compositions is between 0, 1% and 95%, in which connection it must be mentioned that higher concentrations can also be used if the compositions are applied from an aircraft or other appropriate application devices.

The compounds of the formula I can, for example, be formulated as follows:

Dusts

The following substances are used to obtain
a. a 5% and b) a 2% dust:
a. 5 parts of active substance, 95 parts of talcum;
b. 2 parts of active substance, 1 part of highly disperse silicic acid, 97 parts of talcum.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3 - 0.8 mm).
The active substance mixed with epichlorohydrin and the mixture is dissolved in 6 parts of acetone. The polyethylene glycol and cetyl polyglycol ether are then added. The resultant solution is sprayed on kaolin, and the acetone is subsequently evaporated in vacuo.

Wettable powder

The following constituents are used for the preparation of (a) a 40%, (b) and (c) a 25%, and (d) a 10% wettable powder:
a. 40 parts of active substance, 5 parts of sodium ligninsulphonate, 1 part of sodium dibutylnaphthalenesulphonate.
b. 54 parts of silicic acid, 25 parts of active substance, 4.5 parts of calcium ligninsulphonate, 1.9 parts of Champagne chalk-hydroxyethyl cellulose mixture (1:1), 1.5 parts of sodium dibutylnaphthalenesulphonate, 19.5 parts of silicic acid, 19.5 parts of Champagne chalk, 28.1 parts of kaolin.
c. 25 parts of active substance, 2.5 parts of isooctylphenoxy-polyoxyethyleneethanol, 1.7 parts of Champagne chalk/hydroxyethyl cellulose mixture (1:1), 8.3 parts of sodium aluminium silicate, 16.5 parts of kieselguhr, 46 parts of kaolin.
d. 10 parts of active substance, 3 parts of a mixture of the sodium salts of a saturated fatty alcohol sulphates, 5 parts of naphthalenesulphonate acid/formaldehyde condensate, 82 parts of kaolin.

The active substances are intimately mixed in suitable mixers with the additives, and the mixture is then ground in appropriate mills and rollers to yield wettable powders which can be diluted with water to give suspensions of the desired concentration.

Emulsifiable concentrate

The following substances are used to produce a 10% emulsifiable concentrate:
10 parts of active substance,
3.4 parts of epoxidised vegetable oil,
3.4 parts of a combination emulsifier consisting of fatty alcohol polyglycol ether and alkyl aryl sulphonate calcium salt,
40 parts of dimethyl formamide,
43.2 parts of xylene.
By diluting such a concentrate with water it is possible to manufacture emulsions of the desired concentration.

Spray

The following constituents are used to prepare (a) a 5% and (b) a 95% spray:
a. 5 parts of active substance, 1 part of epichlorohydrin, 94 parts of benzene (boiling limits 160° C-190° C.
b. 95 parts of active substance, 5 parts of epichlorohydrin.

The following Examples illustrate the invention in more detail.

EXAMPLE 1

Preparation of 2,2-dimethyl-5-(3,4-dichlorophenylcarbamoyl)-6-hydroxy-m-dioxin-4-one To a solution of 14.4 g of isopropylidene malonate in 150 ml of dimethyl sulphoxide were added dropwise, at room temperature, 10.1 g of triethylamine and thereafter, at 20° to 30° C, 18.8 g of 3,4-dichlorophenylisocyanate in 30 ml of dimethyl sulphoxide. The mixture was reacted for 12 to 15 hours at room temperature and the resultant solution was poured into a solution of 20 ml of concentrated hydrochloric acid in 200 ml of water. The precipitate which formed was collected with suction. Recrystallisation from 130 ml of acetone yielded the product of the formula

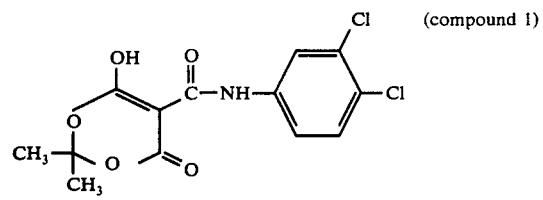

(compound 1)

with a melting point of 132°-134° C.

The following compounds of the formula Ia were obtained in analogous manner:

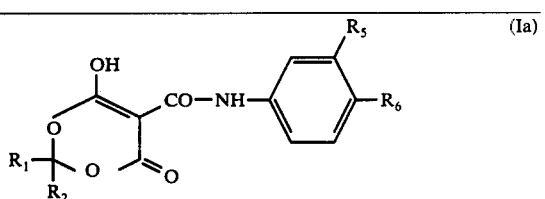

(Ia)

| Compound | $R_1$ | $R_2$ | $R_5$ | $R_6$ | Physical data |
|---|---|---|---|---|---|
| 2 | CH₃ | CH₃ | H | H | m.p. 105° C |
| 3 | CH₃ | CH₃ | Cl | H | m.p. 116° C |
| 4 | CH₃ | CH₃ | H | Cl | m.p. 145-146° C |
| 5 | CH₃ | CH₃ | H | F | m.p. 140° C |
| 6 | —(CH₂)₄— | | H | H | m.p. 108° C |
| 7 | —(CH₂)₄— | | Cl | H | m.p. 126° C |
| 8 | —(CH₂)₄— | | H | Cl | m.p. 151° C |
| 9 | —(CH₂)₄— | | Cl | Cl | m.p. 120° C |
| 10 | —(CH₂)₄— | | H | F | m.p. 142° C |
| 11 | —(CH₂)₅— | | H | H | m.p. 119° C |
| 12 | —(CH₂)₅— | | Cl | H | m.p. 151° C |
| 13 | —(CH₂)₅— | | H | Cl | m.p. 153° C |

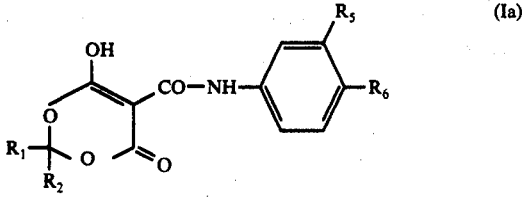

| Compound | $R_1$ | $R_2$ | $R_5$ | $R_6$ | Physical data |
|---|---|---|---|---|---|
| 14 | —(CH$_2$)$_5$— | | Cl | Cl | m.p. 142° C |
| 15 | —(CH$_2$)$_5$— | | H | F | m.p. 138° C |

EXAMPLE 2

Insecticidal stomach poison action (*Leptinotarsa decemlineata*)

Potato plants were sprayed with a 0.05% aqueous emulsion of the compound to be tested (obtained from a 10% emulsifiable concentrate).

After the spray coating had dried, the plants were populated with Leptinotarsa decemlineata larvae in the L$_3$-stage. Two plants were used per test and evaluation of the mortality achieved was made after 2, 4, 8, 24 and 48 hours respectively after the start of the test. The test was carried out at 24° C and 60% relative humidity.

In the above test, compounds of Example 1 exhibited a positive insecticidal stomach poison action on larvae of the species Leptinotarsa decemlineata. Compounds 1, 8, 13 and 14 of Example 1 are to be singled out for their particularly good action (100% kill).

EXAMPLE 3

Inhibition of damage caused by eating (*Leptinotarsa decemlineata*)

Two potato plants (15 cm in height) were sprayed with 25 ml of an acetone/water mixture (1:1) containing 0.01% of test substance.

After the spray coating had dried, each of the potato plants was populated with 10 larvae of the species Leptinotarsa decemlineata (L$_3$-stage). A plastic cylinder was then slipped over each plant to prevent the larvae from migrating. A copper gauze top was used to seal the cylinder. The damage caused by eating was determined 2 days later.

In the above test, compounds of Example 1 effectively reduced damage from eating. Compounds 1, 5, 8, 9, 13 and 14 are to be singled out for their especially good action (only traces of damage were observed).

EXAMPLE 4

Insecticidal stomach poison/contact action (*Anthanomus grandis*)

Cotton plants in pots were sprayed with a spray broth containing 500 ppm of test substance (obtained from a 25% wettable powder) and allowed to dry. Each of the plants was then populated with 5 one-day-old insects of the species Anthanomus grandis and the plants were kept in greenhouse compartments at 24° C and 60% relative humidity.

The number of dead and moribund insects was determined at intervals of 2, 4, 25 and 48 hours respectively after the start of the test. Two plants were used per test substance.

In the above test, the compounds of Example 1 exhibited a good action against insects of the species Anthanomus grandis.

EXAMPLE 5

Action against *Musca domestica*

50 g of freshly prepared CSMA nutrient substrate for maggots were charged into beakers. 5.0; 2.5 or 0.5 ml amounts of a 1% (by weight) acetonic solution of the respective active substance was pipetted onto the nutrient substrate present in the beakers. The substrate was then thoroughly mixed and the acetone subsequently allowed to evaporate over a period of at least 20 hours.

Then 25 one-day-old maggots of *Musca domestica* were put into each of the beakers containing the treated nutrient substrate for testing with each active substance at one of its given concentrations. After the maggots had pupated, the pupae were separated from the substrate by flushing them out with water and then deposited in containers closed with a perforated top.

Each batch of flushed out pupae was counted to determine the toxic effect of the active substance on the maggot development. The number of flies which had hatched out of the pupae was then counted after 10 days and any influence on the metamorphosis thereby determined.

The compounds of the formula I acted well in this test against insects of the species Musca domestica. Compounds 1, 4 and 5 are to be singled out for their particularly good action (100% kill at 0.5 ml).

EXAMPLE 6

Action against *Lucilia sericata*

An aqueous solution containing 0.1% of test substance (2 ml) was added to 2 ml of a culture medium. Approx. 30 freshly hatched-out larvae of *Lucilia sericata* were then added to the culture medium and the insecticidal action was determined after 96 hours by evaluating the mortality rate.

In this test, the compounds of Example 1, especially compounds 1, 2, 4, 6, 9 and 11, acted well against larvae of *Lucilia sericata*.

What is claimed is:

1. A method of killing insects which comprises applying to said insects or the locus thereof an insecticidally effective amount of a compound of the formula

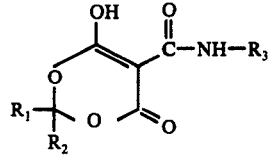

wherein
R$_1$ and R$_2$ are each methyl or together are tetramethylene or pentamethylene and R$_3$ is phenyl, 3-chlorophenyl, 4-chlorophenyl, 3,4-dichlorophenyl or 4-fluorophenyl.

2. The method of claim 1 wherein the compound is 2,2-dimethyl-5-(phenylcarbamoyl)-6-hydroxy-*m*-dioxin-4-one.

3. The method of claim 1 wherein the compound is 2,2-dimethyl-5-(4-chlorophenylcarbamoyl)-6-hydroxy-*m*-dioxin-4-one.

4. The method of claim 1 wherein the locus is growing plants.

5. The method of claim 4 wherein the plants are cotton or vegetable plants.

6. The method of claim 5 wherein the insects are of the species *Anthonomus grandis* or *Leptinotarsa decemlineata*.

7. The method of claim 1 wherein the locus is productive livestock or the locus of such livestock.

8. The method of claim 7 wherein the insects are of the species *Lucilia sericata*.

* * * * *